Sept. 3, 1957 A. MANSUINO Plant Pat. 1,639
ROSE PLANT
Filed Dec. 31, 1956
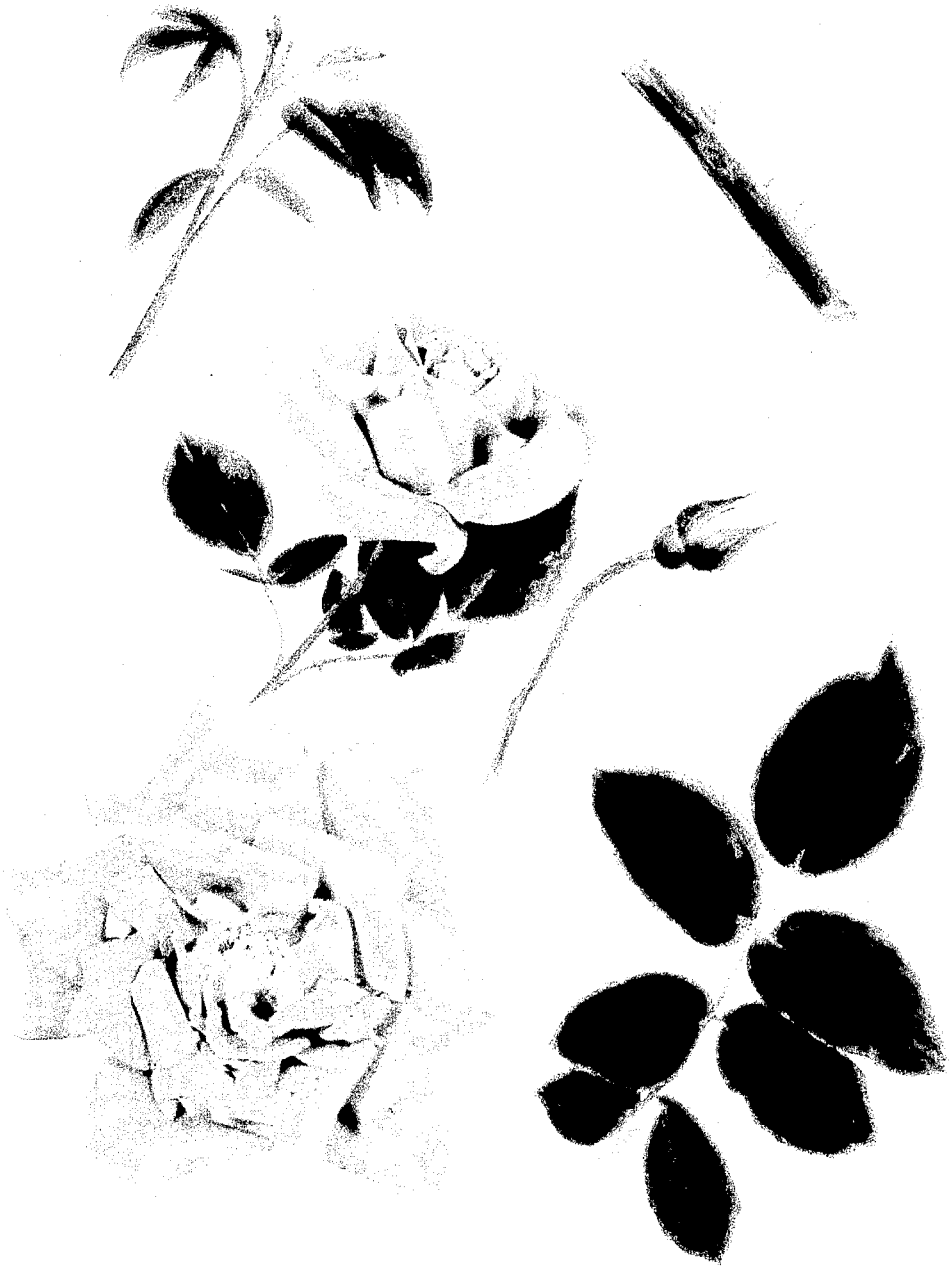
Inventor.
Ada Mansuino
By: Robert Robb
Attorneys.

United States Patent Office

Plant Pat. 1,639
Patented Sept. 3, 1957

1,639

ROSE PLANT

Ada Mansuino, Sanremo, Italy, assignor to Jackson & Perkins Company, Newark, N. Y., a corporation of New York Application December 31, 1956, Serial No. 631,985

1 Claim. (Cl. 47—61)

The present invention relates to a new and distinct variety of rose plant of the hybrid tea class, which was originated by me by crossing the variety "Crimson Glory" (U. S. Plant Patent No. 105) with the variety "Signora" (U. S. Plant Patent No. 201).

The primary objective of this breeding was to produce a new rose variety in which there is combined the vigor of the parent variety "Signora" and the rich red bloom color of "Crimson Glory." This objective was fully achieved, along with other improvements, as evidenced by the following characteristics which are outstanding in the new variety:

(1) Vigorous plant and growth;

(2) Free-blooming habit;

(3) A distinctive Rose Red general color tonality, with the lower half of the petals overcast with Rose color which is accentuated by the Acajou Red color of the young shoots; and (4) The very strong bloom fragrance of "Old Rose Perfume."

The foregoing characteristics definitely distinguish my new variety from its parents, as well as from all other varieties of its class, and asexual reproduction thereof by budding, as performed at Newark, New York, U. S. A., and also at Pleasanton, California, U. S. A., shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
- *Seed parent.*—"Crimson Glory."
- *Pollen parent.*—"Signora."

Classification:
- *Botanic.*—Hybrid tea.
- *Commercial.*—Hybrid tea.

*Flower*

(Observations made from specimens grown outdoors at Newark, New York, U. S. A. about mid-afternoon, near the middle of August.)

Blooming habit: Recurrent—Continuous.

Bud:
- *Size.*—Medium.
- *Form.*—Urn; is not affected by wet or hot weather.
- *Color.*—When sepals first divide—Pomegranate Purple, Plate 12. When petals begin to unfurl—Pomegranate Purple, Plate 12, lightly overcast with Rose Red, Plate 12. When half-blown: inside of petals—Rose Red, Plate 12, lightly overcast with Tyrian Rose, Plate 12; reverse of petals—Tyrian Rose, Plate 12, lightly overcast with Rose Red, Plate 12.
- *Sepals.*—Smooth edge; curl back when petals begin to unfurl. Color: inside—Light Turtle Green, Plate 32; outside—Light Cress Green, Plate 31.
- *Calyx.*—Color—Light Cress Green, Plate 31. Shape—funnel. Size—broad. Aspect—smooth. Odor when rubbed—none.
- *Peduncle.*—Length—medium. Aspect—smooth. Strength—erect; slender. Color—Lettuce Green, Plate 5.
- *Opening.*—Opens up well; is not affected by adverse weather conditions.

Bloom:
- *Size.*—Large. Average size when fully expanded—5 inches.
- *Borne.*—Singly.
- *Stems.*—Medium length; normal strength.
- *Form (when first open).*—Cupped. Permanence—outer petals curl back.
- *Petalage.*—Double (full but open center). Number of petals under normal conditions—25.
- *Color.*—Center of flower—Rose Red, Plate 12. Outer petals—Rose Red, Plate 12, with outer edges of petals and lower half of petals lightly overcast with Rose Color, Plate 12; base of petals (aiglet)—Light Cadmium, Plate 4; inside of petals—Rose Red, Plate 12, with lower half of petals overcast with Rose Color, Plate 12; Reverse of petals—Rose Color, Plate 12, lightly overcast with Rose Red, Plate 12. General tonality from a distance—Rose Red, Plate 12.
- *Discoloration.*—General tonality at end of first day—Rose Red, Plate 12. Second day—Rose Red, Plate 12, lightly overcast with Rose Color, Plate 12. Third day—Rose Red, Plate 12, overcast with Rose Color, Plate 12.

Petals:
- *Texture.*—Leathery; is not affected by wet or hot weather.
- *Appearance.*—Inside—velvety; outside—satiny.
- *Form.*—Oval; slightly notched.
- *Arrangement.*—Imbricated (regularly arranged shingle-like).
- *Petaloids in center.*—Few; large.
- *Persistence.*—Drop off cleanly.
- *Fragrance.*—Very strong. Nature—"Old Rose Perfume" (Centifolia).
- *Lasting quality.*—On the plant—long. As cut flower—long.

*Genital organs*

Stamens, anthers: Medium size; many; regularly arranged around styles. Color—Light Orange-Yellow, Plate 3.

Stamens, filaments (threads): Medium length. Color—Scarlet Red, Plate 1.

Pollen: Color—Pale Yellow-Orange, Plate 3.

Styles: Bunched; uneven length; medium length; thin.

Stigmas: Color—Buff-Yellow, Plate 4.

Ovaries: All enclosed in calyx.

Hips: None.

Seeds: None.

*Plant*

Form: Bush.

Growth: Vigorous; upright.

Foliage: Compound of 5 to 7 leaflets.
- *Size.*—Medium.
- *Quantity.*—Normal.
- *Color.*—New foliage: upper side—Indian Lake, Plate 26; under side—Dahlia Carmine, Plate 26. Old foliage: upper side—Dark Cress Green, Plate 31; under side—Kildare Green, Plate 31.

*Shape.*—Oval.

*Texture.*—Upper side—leathery. Under side—smooth.

*Ribs and veins.*—Ordinary.

*Edge.*—Serrated (saw-toothed).

*Serration.*—Single; small.

*Leaf Stem.*—Color—Spinel Red, Plate 26. Under side—prickly.

*Stipules.*—Medium length; smooth.

Wood:

*New wood.*—Color—Acajou Red, Plate 13. Bark—smooth.

*Old wood.*—Color—Cress Green, Plate 31. Bark—smooth.

Thorns:

*Thorns.*—Quantity: on main stalks from base—Ordinary; on laterals from stalk—Ordinary. Form: narrow base; medium length; hooked downward. Color (when young): Eugenia Red, Plate 13. Position: irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by its vigorous plant and growth, its free-blooming habit, the distinctive Rose Red general color tonality of its blooms, with the lower half of the petals overcast with Rose color and accentuated by the Acajou Red color of the young shoots, and the very strong bloom fragrance of "Old Rose Perfume."

No references cited.